March 26, 1974 A. BARBERET Plant Pat. 3,532
CARNATION PLANT
Filed Dec. 11 1972
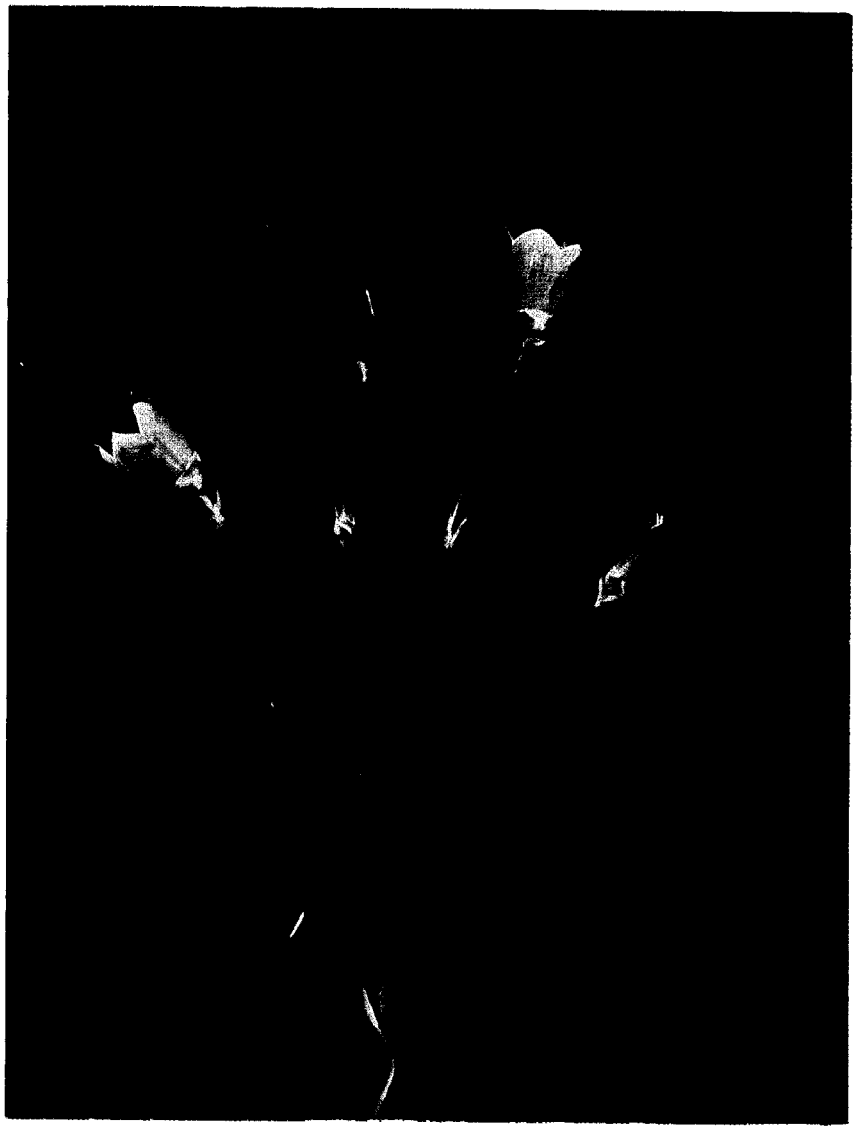

United States Patent Office

Plant Pat. 3,532
Patented Mar. 26, 1974

3,532
CARNATION PLANT

Alexandre Barberet, La Londe, France, assignor to Laboratoire de Physiologie Vegetale de la Londe, Societe Civile, La Londe, France Filed Dec. 11, 1972, Ser. No. 313,746
Claims priority, application Italy, Dec. 23, 1971, 32,848/71
Int. Cl. A01h 5/00
U.S. Cl. Plt.—73 1 Claim

ABSTRACT OF THE DISCLOSURE

A new variety of carnation plant originated as a seedling hybrid of two unnamed and unpatented varieties of Dianthus Caryophyllus, the new variety being distinguished by its good wintertime flower production, and the stable color of its blooms.

BACKGROUND OF THE NEW PLANT

This new variety of carnation plant was developed by me in 1968 at La Londe, France, as a seedling resulting from the cross of two varieties of Dianthus Caryophyllus, both unnamed and unpatented, identified in my records as 6V23 for the seed parent and 6B15 for the pollen parent. My objective was to develop a carnation plant having improved winter flower production and stability of color and this new seedling was selected because it appeared to have the desired characteristics. Asexual propagation of this new plant by cuttings was done by me and under my direction at La Londe, France, and several generations of the new plant demonstrated that the desired characteristics have been achieved and are firmly fixed. This new variety of carnation is now being propagated by means of cuttings and on a commercial scale at La Londe, France, and at West Hartford, Conn.

DESCRIPTION OF THE DRAWINGS

My new variety of carnation plant is illustrated by the accompanying drawings which show the color characteristics of the flower, by photographic reproduction, as nearly true as it is reasonably possible to obtain by conventional commercial photographic procedures.

DESCRIPTION OF THE NEW PLANT

The following is a detailed description of this new variety of carnation plant with color designations according to The RHS Colour Chart published by The Royal Horticultural Society at London, England.

*The plant*

Origin: Seedling
Parentage:
*Seed parent.*—Carnation 6V23 (upatented and unnamed).
*Pollen parent.*—Carnation 6B15 (unpatented and unnamed).
Classification:
*Botanic.*—Hybrid of Dianthus Caryophyllus.
*Commercial.*—Carnation for cut flowers.
Form: Bush. The same as Sim types of carnation plants.
Height: About 60 cm.
Growth: Vigorous and erect, with normal upright branching.
Foliage: Quantity—abundant.
*Leaf shape.*—Lanceolate and from 12 to 16 cm. long.
*Texture.*—Smooth.
*Color.*—Upper side—Green Group 133C. Under side—green.
*Ribs.*—Single and axial.
*Petioles.*—None. Leaf is amplexicaul.

*The bud*

Form: Ovoid.
Size: Medium, Diameter: 22 mm. Length: 32 mm.
Opening: Bud opens slowly.
Color: Light Green when sepals first divide and when petals begin to unfurl.
Sepals: Curl back. Color: Inside—Pale Green. Outside—Light Green.
Calyx: Large and pear shaped.
*Aspect.*—Smooth.
*Splitting.*—Calyx very rarely splits.

*The flower*

Blooming habit: Profuse and continuous the year around.
Size of bloom: Medium, averaging 7.15 cm. in diameter and 4.75 cm. in depth.
Borne: Singly, after disbudding.
Shape: High center when bloom first opens, changing nearer to a dome shape.
Petalage: Number of petals—54 to 75, averaging about 64.
*Form.*—Fan shaped.
*Arrangement.*—Imbricated.
*Color.*—Outer petal—Red Group 53B with base of Red-Purple Group 57A. Inside petals and reverse sides are of the same colors.
*Texture.*—Soft.
*Appearance.*—Satiny.
Petaloids: About 10 in number.
*Size.*—About half the size of the other petals.
*Color.*—Crimson as in the other petals.
Persistence: Blooms hang on and dry.
Fragrance: Just perceptible.
Disease resistance: Plant resists *Fusarium coseum* as observed in the areas where the plant is grown.
Lasting quality: *On the plant.*—15 days. *As cut flower*—10 days.

*Reproductive organs*

Stamens:
*Anthers.*—2 to 3 mm. long and averaging about 10 in number.
*Filaments.*—2.5 cm. long. Color—White and Reddish.
*Pollen.*—Yellowish in color.
Pistils: 2 or 3 in number. 3.5 cm. long when ripe.
*Stigmas.*—White and flushed with Crimson.
Ovaries: Cone shaped.

*Fruit*

Fertility: Slightly fertile.
Shape: Pear shaped.
Color: Greenish and Ochreous at maturity.

This new plant most resembles the variety Joker (unpatented) and its particular advantages are to be found in its good wintertime flower production, the stable color of its blooms from season to season and its production of larger flowers than Joker.

I claim:

1. The new and distinct variety of Dianthus Caryophyllus substantially as herein show and described, characterized in particular by the stable color of its crimson flowers and by its high year around productivity.

No references cited.

ROBERT E. BAGWILL, Primary Examiner